United States Patent

Angerbauer et al.

Patent Number: 4,626,535
Date of Patent: Dec. 2, 1986

[54] CEPHALOSPORINS

[75] Inventors: Rolf Angerbauer; Michael Boberg; Günther Kinast; Karl G. Metzger; Wilfried Schröck, all of Wuppertal; Hans-Joachim Zeiler, Neviges, all of Fed. Rep. of Germany

[73] Assignee: Bayer Aktiengesellschaft, Leverkusen, Fed. Rep. of Germany

[21] Appl. No.: 566,975

[22] Filed: Dec. 30, 1983

[30] Foreign Application Priority Data

Jan. 11, 1983 [DE] Fed. Rep. of Germany ....... 3300593

[51] Int. Cl.$^4$ ................. C07D 501/38; A61K 31/545
[52] U.S. Cl. ..................... 514/203; 514/200; 514/204; 514/206; 540/222; 540/224; 540/225; 540/227; 540/228
[58] Field of Search ....................... 544/25, 22, 27, 24, 544/28; 514/200, 203, 204, 206

[56] References Cited

U.S. PATENT DOCUMENTS 4,390,534  6/1983  Teraji et al. ..................... 544/27
4,463,003  7/1984  Takaya et al. .................... 544/27
4,489,076  12/1984  Kinast et al. ..................... 544/21

Primary Examiner—Nicholas S. Rizzo
Attorney, Agent, or Firm—Sprung Horn Kramer & Woods

[57] ABSTRACT

Novel antibacterially active cephalosporins of the formula

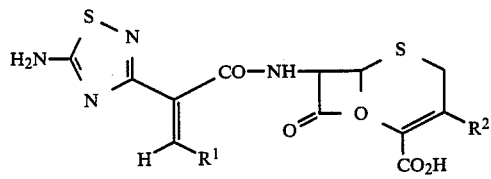

in which
$R^1$ denotes hydrogen, optionally substituted alkyl, a substituted or unsubstituted phenyl ring, a polycyclic aromatic ring or an optionally substituted heterocyclic 5- or 6-member ring having 1-4 heteroatoms,
$R^2$ represents hydrogen, $C_1$-$C_4$-alkyl, $C_1$-$C_4$-alkenyl, halogen, $C_1$-$C_4$-alkoxy, $C_1$-$C_4$-alkylthio, hydroxymethyl, formyloxymethyl, $C_1$-$C_4$-alkylcarbonyloxymethyl, aminocarbonyloxymethyl, pyridiniummethyl, 4-carbamoylpyridiniummethyl, 4-sulphonylethylpyridiniummethyl, 4-carboxylmethylpyridiniummethyl or heterocyclylthiomethyl, heterocyclyl representing a radical of the formula

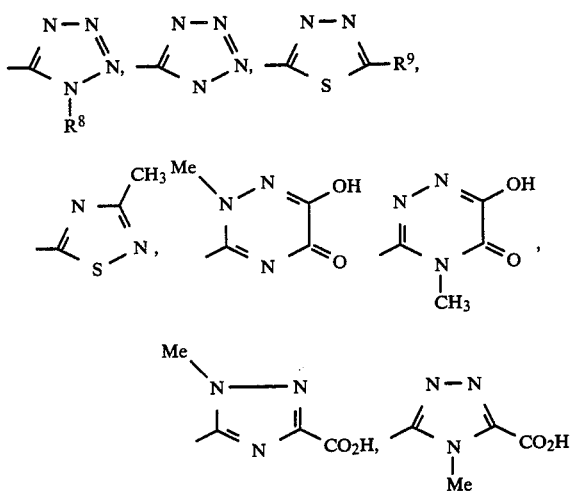

wherein
$R^8$ denotes hydrogen, methyl, 2-dimethylaminoethyl, carboxymethyl, sulphomethyl, carboxyethyl or sulphoethyl and
$R^9$ denotes hydrogen or methyl,
or pharmaceutically tolerated salts or esters thereof.

12 Claims, No Drawings

CEPHALOSPORINS

The invention relates to new cephalosporins, their use as medicaments, especially in antibacterial therapy, and processes for their preparation.

Cephalosporins of the general formula I are made available by the invention.

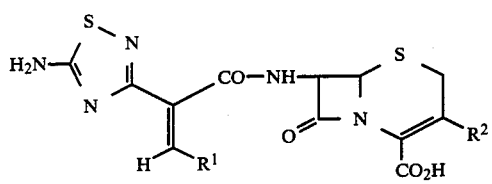 (I)

In the general formula I, $R^1$ denotes hydrogen, optionally substituted alkyl, a substituted or unsubstituted phenyl ring, a polycyclic aromatic ring or an optionally substituted heterocyclic 5- or 6-member ring having 1-4 heteroatoms, and $R^1$ particularly denotes $C_1-C_{12}$-alkyl, phenyl or halogen-substituted phenyl.

In addition, $R^2$ denotes hydrogen, $C_1-C_4$-alkyl, $C_1-C_4$-alkenyl, halogen, $C_1-C_4$-alkoxy, $C_1-C_4$-alkylthio, hydroxymethyl, formyloxymethyl, $C_1-C_4$-alkylcarbonyloxymethyl, aminocarbonyloxymethyl, pyridiniummethyl, 4-carbamoylpyridiniummethyl, 4-sulphonylethylpyridiniummethyl, 4-carboxylmethylpyridiniummethyl or heterocyclylthiomethyl, heterocyclyl preferably representing a radical of the formula

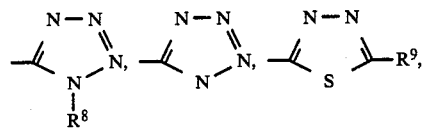

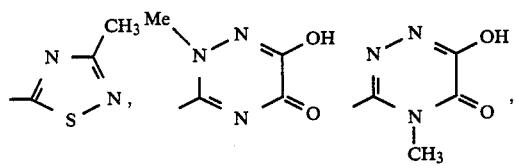

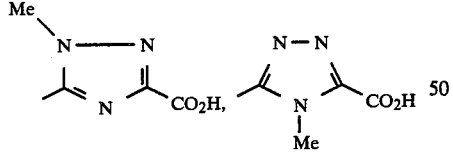

wherein $R^8$ denotes hydrogen, methyl, 2-dimethylaminoethyl, carboxymethyl, sulphomethyl, carboxyethyl or sulphoethyl and $R^9$ denotes hydrogen or methyl.

The compounds of the formula I have the Z configuration according to the E/Z nomenclature described in J. Amer. Chem. Soc. 90, 509 (1968).

The compounds of the formula I can be present as free acids, esters, as internal salts or as non-toxic, pharmaceutically tolerated salts of the acid carboxyl group, such as the sodium, potassium, magnesium, calcium, aluminum and ammonium salts, and non-toxic substituted ammonium salts, with amines such as di- and tri-lower-alkylamines, procaine, dibenzylamine, N,N'-dibenzylethylenediamine, N-benzyl-β-phenylethylamine, N-methylmorpholine and N-ethylmorpholine, 1-ephenamine, dehydroabietylamine, N,N'-bis-dehydroabietylethylenediamine, N-lower-alkylpiperidine and other amines which can be used for forming salts of penicillins or cephalosporins.

Those compounds in the Z configuration are preferred in which $R^2$ denotes a radical H, Cl, $OCH_3$, $-CH_2OCOCH_3$, $CH_2-O-CONH_2$,

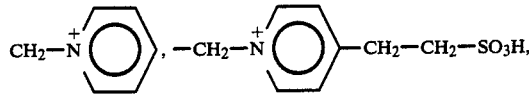

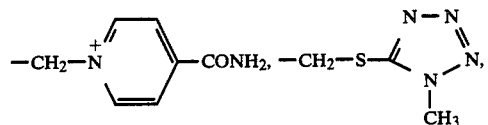

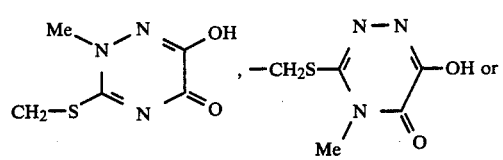

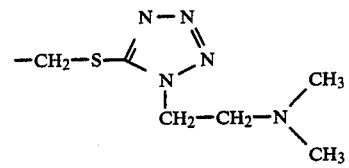

and $R^1$ denotes $C_1$ to $C_6$ alkyl.

The compounds of the formula I are obtained by converting the acids of the formula II, in which $R^4$ represents a customarily used protective group, into the mixed anhydrides of the formula III, reacting the latter with the compounds of the formula IV, and then splitting off the protective group $R^4$ from the resulting compounds of the formula V.

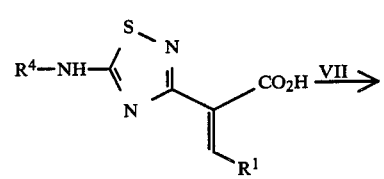

II

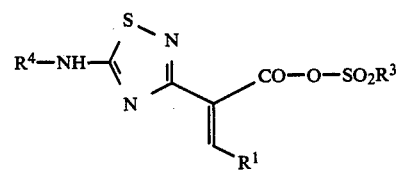

III

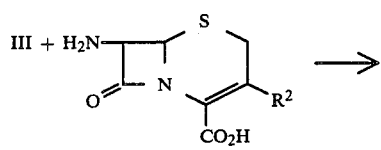

IV

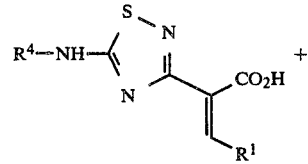

II

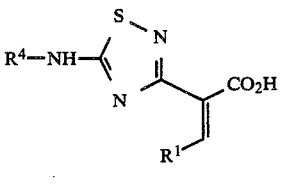

IIa

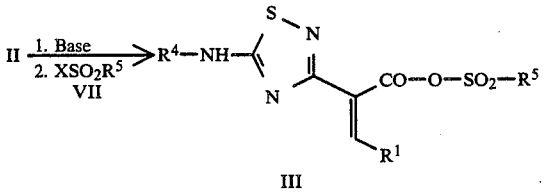

III

The compounds of the formula IX are obtained from known compounds of the formula XIII (European Pat. No. 22,245) by esterifying and splitting off the N-protective group with, for example, trifluoroacetic acid.

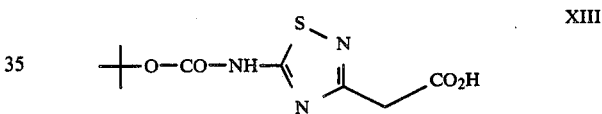

XIII $R^4$ denotes $R^7$—O—CO, and $R^6$ and $R^7$ can be different or identical and denote an optionally substituted alkyl, cycloalkyl, alkenyl, cycloalkenyl, aryl or heterocyclyl radical, heteroatoms as substituents of the radicals and double bonds in the alkenyl and cycloalkenyl radicals being separated from the oxycarbonyl group by at least one C atom.

In particular, $R^6$ and $R^7$ are an optionally substituted alkyl radical having 1–15 C atoms, an optionally substituted alkenyl radical having 3–15 C atoms, an optionally substituted cycloalkyl radical having 3–10 C atoms, an optionally substituted cycloalkenyl radical having 5–10 C atoms, an optionally substituted aryl radical having 1–3 rings or an optionally substituted heterocyclyl radical having 1–3 rings which can contain up to 5 nitrogen, sulphur or oxygen atoms.

The alkyl, alkenyl, cycloalkyl and cycloalkenyl radicals mentioned can be substituted by alkyl radicals having 1–4 C atoms, O-alkyl radicals having 1–4 C atoms, halogen, preferably chlorine, optionally substituted phenyl radicals, C≡N and $C_1$-$C_5$-trialkylsilyl.

All aryl and heterocyclyl radicals, including the phenyl radicals mentioned, can be substituted by alkyl, O-alkyl, S-alkyl, alkyloxycarbonyl, halogen and phenyl radicals, it being possible for all alkyl radicals to have 1–4 C atoms, and by nitro and C≡N.

When the radicals $R^6$ and $R^7$ are substituted, preferably by the abovementioned substituents, then they can carry 1–5, preferably 1 or 2, substituents.

It is particularly advantageous for the process when

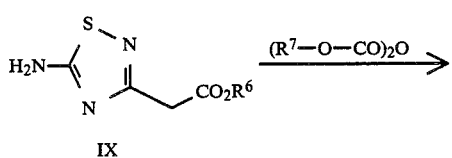

V

It is advantageous for the process to use as $R^4$ an acid-labile protective group, such as, for example, tert.-butyloxycarbonyl, trityl or formyl, and to split off the $R^4$ in V with, for example, trifluoroacetic acid or formic acid.

It is also advantageous to select $R^5$=$CH_3$.

The compounds II and III can be prepared in accordance with the diagram below.

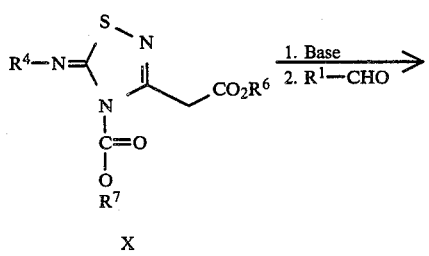

IX

X

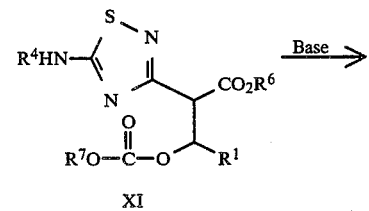

XI

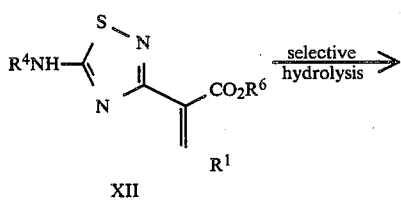

XII $R^4$ is a protective group which is stable in base and is split off in acid, such as, for example, tert.-butoxycarbonyl, and when $R^6$ is a radical which is hydrolyzed by base, such as, for example, methyl or ethyl.

The compounds of the formula X are obtained by allowing the compounds of the formula IX to react with a pyrocarbonic ester of the formula $R^7$—O—CO—O—CO—O—$R^7$ in a suitable solvent.

Particularly suitable solvents are aprotic polar solvents, such as, for example, acetonitrile, dimethylformamide, hexamethylphosphoric triamide or dimethyl sulphoxide, particularly the two latter. The reaction takes place particularly advantageously at room temperature or at lower temperatures, for example, 10° to −50° C., the components being allowed to react together for 1–7 days. The pyrocarbonic acid is generally employed with 2–2.5 mole-equivalents.

In order to prepare the compounds of the formula XI, 1 to 1.1 equivalents of a base are added to the compounds of the formula X in a suitable solvent at low temperatures, and then 1 to 1.2 equivalents of an aldehyde of the formula $R^1$—CHO are added.

Examples of solvents which can be used for the reaction are dimethylformamide, dimethyl sulphoxide, diethyl ether, tetrahydrofuran or toluene, preferably tetrahydrofuran, and of bases, alcoholates, hydrides, amides or organometallics, preferably potassium tert.-butylate, lithium diisopropylamide and butyllithium. In order to carry out the reaction, the base is added, at −50° to −80° C., to a solution of X and then, at −50° to −60° C., the aldehyde is added and the mixture is stirred at −50° to −60° C. for about 12 hours. The mixture is neutralized and worked up to isolate the products of the formula XI.

In the compounds of the formula XI, $R^4$, $R^6$ and $R^7$ have the meanings previously detailed, and $R^1$ has the meaning indicated in the introduction.

In order to carry out the process for the preparation of the compounds of the formula I, it is unnecessary to isolate the compounds of the formula XI. On the contrary, it is advantageous to convert them directly in situ into the compounds of the formula XII. It is generally sufficient for this purpose to allow the mixture, after addition of the aldehyde $R^1$—CHO, to warm to room temperature and to stir it overnight at room temperature. If the elimination of XI to give XII is not complete by then, 1 to 1.2 equivalents of a base, such as, for example, a hydride, an alcoholate or an amide, in particular potassium tert.-butylate, are added and the mixture is stirred at room temperature for about 10 hours.

On the other hand, if the compound of the formula XI has already been isolated, then to prepare the compounds of the formula XII, 1.1 to 2.2 equivalents of a base are added to a solution of the compounds of the formula XI in a suitable solvent. The solvent and base mentioned for the reaction of X to give XI can be used, preferably tetrahydrofuran and potassium tert.-butylate.

The compounds of the formula XII are obtained in mixtures of E and Z isomers which can be separated, for example, by recrystallization or by column chromatography on silica gel.

In the compounds of the formula XII, $R^1$, $R^4$ and $R^6$ have the same meanings as in the compounds of the formula XI.

For the preparation of the Z carboxylic acids of the formula II, the Z esters which can be obtained by separating the mixture of E and Z isomers of the esters of the formula XII can be hydrolyzed. However, it is more favorable for carrying out the process for the preparation of the compounds of the formula I selectively to hydrolyze the mixture of E and Z isomers of the esters of the formula XII in such a manner that, under mild conditions, first the E esters are converted into the E carboxylic acids of the formula IIa and separated off and then the remaining Z esters, in which the ester group is subject to greater steric shielding, are hydrolyzed under drastic conditions to give the Z carboxylic acids of the formula II.

Examples of the mild hydrolysis conditions which lead to the E carboxylic acids IIa are ethanol/2N sodium hydroxide solution/room temperature/24 hours. The hydrolysis is advantageously carried out in such a manner that, after conversion of the compounds of the formula XI into the compounds of the formula XII, 2N sodium hydroxide solution is immediately added to the reaction mixture and it is stirred at room temperature or with gentle heating until the E esters are hydrolyzed. Then, the Z esters are removed from the mixture by extraction under alkaline conditions and they are hydrolyzed under more drastic conditions.

Examples of more drastic hydrolysis conditions are ethanol/2N sodium hydroxide solution/24 hours reflux, and if necessary more concentrated sodium hydroxide solution or higher boiling solvents, such as, for example, dioxane.

The desired Z carboxylic acids of the formula II and the E carboxylic acids of the formula IIa are obtained in this manner.

When the mixture of E and Z isomers of the carboxylic acids II and IIa is available, the Z carboxylic acids of the formula II can be isolated pure by, for example, crystallization or by separation on an ion exchanger. Separation using ion exchangers is simple since the Z carboxylic acids of the formula II are very much stronger acids than the E carboxylic acids of the formula IIa. Thus the E carboxylic acids of the formula IIa are eluted even with methanol from weakly basis ion exchangers, while the Z carboxylic acids of the formula II are only eluted after addition of electrolytes, for example, 2N sodium hydroxide solution. Weakly basic ion exchangers are understood to be those ion exchangers in the solid or liquid form which contain tertiary amino groups, such as, for example, Lewatit MP 62.

In the compounds of the formula II and IIa, $R^1$ and $R^4$ have the same meaning as for the compounds of the formula XII. In addition, $R^4$ can be H when, before the hydrolysis, $R^4$ in the compounds of the formula XII was a protective group which can be hydrolyzed by alkali, such as, for example, methyloxycarbonyl. However, for carrying out the process for the preparation of the compounds of the formula I, it is more advantageous when $R^4$ is a protective group which is stable under the hydrolysis conditions, preferably tert.-butyloxycarbonyl.

The carboxylic acids of the formula II can also be obtained by reacting the compounds of the formula XIV which are known per se (European Pat. No. A 22,245),

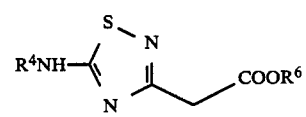

XIV in which $R^4$ and $R^6$ have the abovementioned meaning, with aldehydes of the formula $R^1$—CHO, in which $R^1$ has the abovementioned meaning, in the presence of a mild base, such as, for example, sodium acetate, to give the compounds of the general formula XV

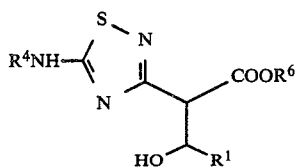

XV and then converting the latter, with an agent which splits off water, such acetyl chloride or thionyl chloride, into the compounds of the general formula XII, from which the compounds of the formula II and IIa are then obtained by selective hydrolysis, or their mixtures are obtained by non-selective hydrolysis.

Moreover, the carboxylic acids of the formula II can be obtained from the carboxylic acids of the formula IIa by isomerization with strong bases, such as, for example, potassium t-butylate in an anhydrous aprotic solvent, such as, for example, dimethylformamide or dimethyl sulphoxide, and subsequent separation out of the carboxylic acids of the formula IIa which are still present in the thereby resulting E/Z mixture by crystallization, chromatography or liquid/liquid partition.

A large number of methods are known in the chemistry of cephalosporins for coupling carboxylic acids to 7-aminocephalosporanic acids, these methods being derived, in the final analysis, from peptide chemistry. However, on attempting to form the amide bond between the Z carboxylic acids of the formula II and the cephalosporanic acids of the formula XV, these methods fail or lead to only very poor yields, particularly when $R^1$ is an alkyl radical. The reasons for this are in the large steric hindrance of the carboxyl group in the carboxylic acids of the formula II by the radical $R^1$ and in the pronounced tendency of the radical $R^1$ to isomerize to the E form after activation of the carboxyl function, for example conversion into the acid chloride.

However, the Z carboxylic acids of the formula II can be activated in a simple, mild and low-cost manner by converting them into the mixed anhydrides of the formula III at low temperatures.

Such mixed anhydrides of the formula III can be prepared by dissolving the carboxylic acid II and a suitable amine in equimolar amounts in a suitable solvent and allowing them to react with 1 to 1.05 equivalents of a sulphonic acid derivative of the formula VII.

All solvents which are stable under the reaction conditions are suitable as solvents, such as, for example, diethyl ether, tetrahydrofuran, acetonitrile, acetone, methylene chloride, chloroform or dimethylformamide.

Suitable amines are tertiary amines, such as, for example, triethylamine or tributylamine, but also sterically hindered secondary amines, such as, for example, diisopropylamine.

The reactions can be carried out at temperatures between −80° C. and room temperature, low temperatures preventing isomerization of the substituents on the double bond. The reactions are advantageously carried out at −20° to −50° C. with a reaction time of from 10 minutes to 10 hours.

The compounds of the formula III can be isolated by working, for example, in tetrahydrofuran as the solvent and with triethylamine as the base, filtering off the resulting triethylamine hydrochloride with suction and removing the solvent by distillation in vacuo. However, it is more advantageous to react the resulting solutions of the compounds of the formula III directly with the cephalosporins of the formula IV. For this purpose, the cephalosporins of the formula IV or their salts are dissolved in a suitable solvent containing 1–4 equivalents of an amine, the solution is precooled to the desired temperature for the subsequent reaction, and this solution at this temperature is added to the solution described above of the compound of the formula III. In order to prevent isomerization of the radical $R^1$ in the reaction products of the formula V, the reaction is advantageously carried out at −60° to −30° C., and the mixture is allowed to come to room temperature overnight.

The solvents mentioned for the preparation of the compounds of the formula III can be used to dissolve the compounds of the formula IV, and the amines mentioned there can be used as the base.

However, if the solubility of the compounds of the formula IV in these solvents is limited, in such a case it is possible advantageously to silylate in a manner known per se or to work with water as the solvent.

X denotes Cl, Br or $OSO_2R^5$, and $R^5$ denotes an alkyl radical having 1–10 C atoms which can optionally be substituted by fluorine, chlorine, CN, phenyl, alkoxycarbonyl, alkyloxy or alkyl, it being possible for the latter alkyl radicals to have 1–4 C atoms, and a phenyl radical which can optionally be substituted by fluorine, chlorine, bromine, CN, alkyl, alkyloxy, alkylthio, alkyloxycarbonyl, it being possible for the latter alkyl groups to have 1–4 C atoms, nitro, trifluoromethyl and phenyl.

$R^5$ very particularly represents a methyl or p-tolyl radical.

It is particularly advantageous to convert the carboxylic acids VI having no protective group into the mixed anhydrides of the formula VIII with the sulphonic acid derivatives VII, and to react the anhydrides directly with IV to give the compounds of the formula I.

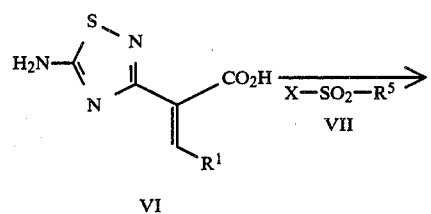

VI

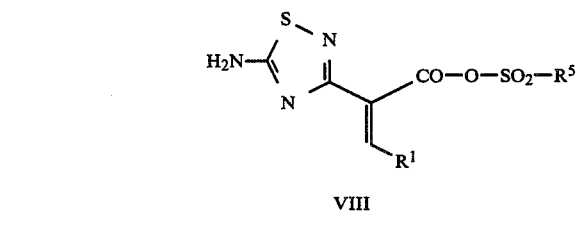

VIII

VIII + IV $\xrightarrow{\text{Base}}$ I

In the compounds VII and VIII, $R^5$ have the abovementioned meanings.

The mixed anhydrides of the formula VIII are prepared in analogy to the anhydrides of the formula III by dissolving the carboxylic acids of the formula VI and 1-1.4 equivalents of an amine in a solvent and allowing them to react with 1 to 1.2 equivalents of a sulphonic acid derivative of the formula VII.

All solvents which are stable under the reaction conditions are suitable as solvents, such as, for example, diethyl ether, tetrahydrofuran, acetonitrile, acetone, methylene chloride, chloroform or dimethylformamide.

Tertiary amines are suitable as the amine, such as, for example, triethylamine or tributylamine, but sterically hindered secondary amines, such as, for example, diisopropylamine are also suitable.

The reactions can be carried out at temperatures between $-80°$ C. and room temperature, low temperatures preventing isomerization of the substituents on the double bond.

The solvents mentioned for the preparation of the compounds of the formula VIII can be used to dissolve the compounds of the formula IV, and the amines mentioned there can be used as the base.

If the solubility of the compounds of the formula IV in these solvents is limited, it is possible in such a case advantageously to silylate in a manner known per se or to work with water as a solvent.

The compounds of the formula VI are obtained by splitting off the protective group $R^4$ from the compounds of the formula II.

The compounds according to the invention exhibit a potent and wide antimicrobial efficacy, particularly for Gram-negative and Gram-positive bacteria. These properties make it possible to use them as chemotherapeutic active compounds in medicine. Using them, the diseases caused by Gram-negative and Gram-positive bacteria and bacterioid micro-organisms can be prevented, alleviated and/or cured.

The compounds according to the invention are particularly effective against bacteria and bacterioid micro-organisms. Thus, they are particularly well suited for the prophylaxis and chemotherapy of local and systemic infections in human and veterinary medicine which are caused by these pathogens.

For example, it is possible to treat and/or prevent local and/or systemic diseases which are caused by the pathogens below or by mixtures of the pathogens below:

Micrococcaceae, such as staphylococci, for example *Staphylococcus aureus, Staph. epidermidis, Staph. aerogenes* and *Gaffkya tetragena* (Staph.=Staphylococcus); Lactobacteriaceae, such as streptococci, for example *Streptococcus pyogenes*, α- and β-haemolytic streptococci, not (γ-)-haemolytic streptococci, *Str. viridans, Str. faecalis* (enterococci) and *Dipolococcus pneumoniae* (pneumococci) (Str.=Streptococcus);

Enterobacteriaceae, such as escherichiae bacteria of the coli group: escherichia bacteria, for example *Escherichia coli*, enterobacter bacteria, for example *E. erogenes, E. cloacae*, klebsiella bacteria, for example *K. pneumoniae*, serratia, for example *Serratia marcescens (E.=Enterobacter) (K.=Klebsiella)*, proteae bacteria of the proteus group: proteus, for example *Proteus vulgaris, Pr. morganii, Pr. rettgeri, Pr. mirabillis* (Pr.=Proteus);

Pseudomonadaceae, such as pseudomonas bacteria, for example *Pseudomonas aeruginosa* (Ps.=Pseudomonas); Bacteroidaceae, such as bacteroides bacteria, for example *Bacteroides fragilis* (B.=Bacteroides).

The above list of pathogens is to be taken merely as exemplary and by no means as restrictive.

Examples of diseases which can be prevented, alleviated and/or cured by the compounds according to the invention which may be mentioned are:

Diseases of the respiratory tract and the pharyngeal cavity;

Otitis; pharyngitis; pneumonia; peritonitis; pyelonephritis; cystitis; endocarditis; systemic infections; bronchitis; arthritis; local infections.

The present invention includes pharmaceutical formulations which, in addition to non-toxic, inert pharmaceutically suitable vehicles, contain one or more compounds according to the invention or which consist of one or more active compounds according to the invention, and processes for the preparation of these formulations.

The present invention also includes pharmaceutical formulations in dosage units. This means that the formulations are in the form of individual parts, for example tablets, coated tablets, capsules, pills, suppositories and ampules, in which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles, there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical formulations.

Tablets, coated tablets, capsules, pills and granules can contain the active compound or compounds alongside the customary vehicles, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium or magnesium stearate and solid polyethylene glycols, or mixtures of these substances listed under (a) to (i).

The tablets, coated tablets, capsules, pills and granules can be provided with the customary coatings and shells, optionally containing opacifying agents, and can also be of such composition that they release the active compound or compounds, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a micro-encapsulated form.

Suppositories can contain, in addition to the active compound or compounds, the customary water-soluble or water-insoluble vehicles, for example polyethylene glycols, fats, for example cacao fat, and higher esters (for example C$_{14}$-alcohol with C$_{16}$-fatty acid) or mixtures of these substances.

For parenteral administration, the solutions and emulsions can also be in a sterile form which is isotonic with blood.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutically active compounds in addition to the compounds according to the invention.

The abovementioned pharmaceutical formulations are prepared in the usual manner according to known methods, for example by mixing the active compound or compounds with the vehicle or vehicles.

The active compounds or the pharmaceutical formulations can be administered topically, orally, parenterally, intraperitonally and/or rectally, preferably orally or parenterally, such as intravenously or intramuscularly.

In general, it has proved advantageous both in human medicine and in veterinary medicine to administer the active compound or compounds in total amounts of about 1 to about 1,000, preferably 1 to 200, mg/kg of body weight every 24 hours, optionally in the form of several individual administrations, in order to achieve the desired results. An individual administration contains the active compound or compounds preferably in amounts of about 1 to about 250, especially of 1 to 60, mg/kg of body weight. However, it can be necessary to deviate from the dosages mentioned, and in particular to do so as a function of the nature and body weight of the subject to be treated, the nature and severity of the illness, the nature of the formulation and of the administration of the medicament, and the time or interval over which the administration takes place. Thus, it can suffice in some cases to manage with less than the abovementioned amount of active compound, whereas in other cases the abovementioned amount of active compound must be exceeded. The particular required optimum dosage and the type of administration of the active compounds can easily be decided by anyone skilled in the art, on the basis of this expert knowledge.

The compounds according to the invention can be combined with another β-lactam antibiotic or with aminoglycoside antibiotics, such as, for example, gentamicin, sisomicin, kanamicin, amikacin or tobramicin, with the objective of broadening the spectrum of action.

The compound of Example 21 was compared in vitro with Cefotaxim (MIC-comparison in Isosensitest agar):

| strain | MIC (mcg/ml) | |
| --- | --- | --- |
| | product | Cefotaxim |
| Staph. 1756 | 8 | 128 |
| Staph. 133 | 0.5 | 1 |
| Staph. 25470 | 8 | >128 |
| Staph. E | 0.125 | 0.5 |
| Psdm. F 41 | 8 | 16 |
| Psdm. Walter | 8–16 | 16 |
| Psdm. 7035 | 8 | 16 |
| Enterobacter Cloacae 56US | 64 | >128 |

EXAMPLE 1

Ethyl 5-tert.-butoxycarbonylimino-4-tert.-butoxycarbonyl-1,2,4-thiadiazol-5-in-3-ylacetate 186 g (1 mole) of ethyl 5-amino-1,2,4-thiadiazol-3-ylacetate, 300 ml of dimethyl sulphoxide and 500 g (2.3 moles) of 98% pure di-tert.-butyl pyrocarbonate are stirred at room temperature for 7 hours. Then, cooling in ice to a maximum of 20° C., 3.5 liters of ice-water are added, the mixture is stirred for 30 min cipitate is filtered off with suction, washed with 2 liters of water and taken up in 2 liters of methylene chloride. The water is separated off, and the methylene chloride phase is dried over Na$_2$SO$_4$ and evaporated in a rotary evaporator.

EXAMPLE 2

1-(5-tert.-Butoxycarbonylamino-1,2,4-thiadiazol-3-yl)-1-(Z)-propenecarboxylic acid 0.145 mole of ethyl 5-tert.-butoxycarbonylimino-4-tert.-butoxycarbonyl-1,2,4-thiadiazol-5-in-3-ylacetate and 400 ml of anhydrous tetrahydrofuran are initially introduced under nitrogen and, at −60° to −50° C., 0.16 mole of n-butyllithium in hexane (15% strength, 100 ml) is added dropwise. Then 9.55 ml (0.17 mole) of acetaldehyde are immediately added, and the mixture is stirred at −60° C. for 10 minutes and then at room temperature overnight. Then 250 ml of 2N sodium hydroxide solution are added and the two-phase mixture is vigorously stirred at room temperature for 24 hours. The tetrahydrofuran is then distilled out at room temperature in vacuo, and the alkaline phase is extracted 2×100 ml of methylene chloride. By acidification of the aqueous phase to pH 2–3 and extraction, 1-(5-tert.-butoxycarbonylamino-1,2,4-thiadiazol-3-yl)-1(E)-propenecarboxylic acid is obtained.

The methylene chloride phase is evaporated in vacuo, and the residue is taken up in 250 ml of ethanol, 250 ml of 2N sodium hydroxide solution are added and the mixture is heated at 60° C. for 24 hours.

After removal of the ethanol by distillation, the alkaline phase is extracted 1×100 ml of methylene chloride, the extract is discarded, and the alkaline phase is acidified to pH 2–3 and the desired 1-(5-tert.-butoxycarbonylamino-1,2,4-thiadiazol-3-yl)-1(Z)-propenecarboxylic acid is extracted with methylene chloride.

EXAMPLE 3

1-(5-tert.-Butoxycarbonylamino-1,2,4-thiadiazol-3-yl)-1(Z)-butenecarboxylic acid Preparation in analogy to Example 2 using propanal instead of acetaldehyde.

EXAMPLE 4

1-(5-tert.-Butoxycarbonylamino-1,2,4-thiadiazol-3-yl)-1(Z)-pentenecarboxylic acid Preparation in analogy to Example 2 using butanal instead of acetaldehyde.

EXAMPLE 5

1-(5-tert.-Butoxycarbonylamino-1,2,4-thiadiazol-3-yl)-1(Z)-hexenecarboxylic acid Preparation in analogy to Example 2 using pentanal instead of acetaldehyde.

EXAMPLE 6

1-(5-tert.-Butoxycarbonylamino-1,2,4-thiadiazol-3-yl)-1(Z)-heptenecarboxylic acid Preparation in analogy to Example 2 using hexanal instead of acetaldehyde.

EXAMPLE 7

1-(5-tert.-Butoxycarbonylamino-1,2,4-thiadiazol-3-yl)-1(Z)-octenecarboxylic acid Preparation in analogy to Example 2 using heptanal instead of acetaldehyde.

EXAMPLE 8

1-(5-tert.-Butoxycarbonylamino-1,2,4-thiadiazol-3-yl)-3-methyl-1(Z)-butenecarboxylic acid Preparation in analogy to Example 2 using isobutyraldehyde instead of acetaldehyde.

EXAMPLE 9

1-(5-tert.-Butoxycarbonylamino-1,2,4-thiadiazol-3-yl)-4-methyl-1(Z)-pentenecarboxylic acid Preparation in analogy to Example 2 using isovaleraldehyde instead of acetaldehyde.

EXAMPLE 10

1-(5-tert.-Butoxycarbonylamino-1,2,4-thiadiazol-3-yl)-3-cyclohexyl-(Z)-acrylic acid Preparation in analogy to Example 2 using cyclohexylaldehyde instead of acetaldehyde.

EXAMPLE 11

7-(1-(5-Amino-1,2,4-thiadiazol-3-yl)-1(Z)-propenecarboxamido-3-acetoxymethyl)-3-cephem-4-carboxylic acid 0.005 mole (1.42 g) of 1-(5-tert.-butoxycarbonylamino-1,2,4-thiadiazol-3-yl)-1(Z)-propenecarboxylic acid and 0.0055 mole (0.76 ml) of triethylamine are dissolved in 20 ml of anhydrous methylene chloride, the solution is cooled to −50° C., 0.0051 mole (0.40 ml) of methanesulphonyl chloride is added, and the mixture is stirred at −50° to −40° C. for 2 hours.

Then a solution, which has been precooled to −50° C., of 0.006 mole (1.63 g) of 3-acetoxymethyl-7-amino-3-cephem-4-carboxylic acid and 0.013 mole (1.80 ml) of triethylamine in 20 ml of anhydrous methylene chloride is added, and the mixture is allowed to warm to room temperature within 12 hours.

For work-up, the mixture is washed twice with 10 ml of H₂O each time, and 40 ml of H₂O are placed on top of the methylene chloride phase and, with stirring and cooling in ice, acidified to pH 2–3 with 1N HCl. The organic phase is separated off, the H₂O phase is extracted 2×20 ml of methylene chloride, and the combined methylene chloride phases are washed with saturated NaCl solution, dried over Na₂SO₄ and evaporated in a rotary evaporator in vacuo. The tert.-butoxycarbonyl-protected cephalosporin is obtained in almost quantitative yield.

10 ml of trifluoroacetic acid are added to the BOC-protected cephalosporin and the mixture is stirred for 30 minutes at room temperature. The trifluoroacetic acid is then removed in vacuo at room temperature, 20 ml of methanol/H₂O 10:1 are added to the residue, followed by 10% strength NaHCO₃ solution until a clear solution of pH 6–7 is introduced. Then pH 3 is set up slowly with 1N HCl, the methanol is slowly removed in vacuo and, if necessary, the pH is again adjusted to 3. The precipitated product is filtered off with suction.

EXAMPLE 12

7-(1-(5-Amino-1,2,4-thiadiazol-3-yl)-1(Z)-propenecarboxamido)-3-(1-methyl-1H-tetrazol-5-yl)thiomethyl-3-cephem-4-carboxylic acid Preparation in analogy to Example 11 from 1-(5-tert.-butoxycarbonylamino-1,2,4-thiadiazol-3-yl)-1(Z)-propenecarboxylic acid and 7-amino-3-(1-methyl-1H-tetrazol-5-yl)thiomethyl-3-cephem-4-carboxylic acid.

EXAMPLE 13

7-(1-(6-Amino-1,2,4-thiadiazol-3-yl)-1(Z)-butenecarboxamido)-3-acetoxymethyl-3-cephem-4-carboxylic acid Preparation in analogy to Example 11 from 1-(5-tert.-butoxycarbonylamino-1,2,4-thiadiazol-3-yl)-1(Z)-butenecarboxylic acid and 3-acetoxymethyl-7-amino-3-cephem-4-carboxylic acid.

EXAMPLE 14

7-(1-(5-Amino-1,2,4-thiadiazol-3-yl)-1(Z)-butenecarboxamido)-3-(1-methyl-1H-tetrazol-5-yl)thiomethyl-3-cephem-4-carboxylic acid Preparation in analogy to Example 11 from 1-tert.-butoxycarbonylamino-1,2,4-thiadiazol-3-yl)-1(Z)-butenecarboxylic acid and 7-amino-3-(1-methyl-1H-tetrazol-5-yl)thiomethyl-3-cephem-4-carboxylic acid.

EXAMPLE 15

7-(1-(5-Amino-1,2,4-thiadiazol-3-yl)-1(Z)-heptenecarboxamido)-3-acetoxymethyl-3-cephem-4-carboxylic acid Preparation in analogy to Example 11 from 1-(5-tert.-butoxycarbonylamino-1,2,4-thiadiazol-3-yl)-1(Z)-heptenecarboxylic acid and 3-acetoxymethyl-7-amino-3-cephem-4-carboxylic acid.

EXAMPLE 16

7-(1-(5-Amino-1,2,4-thiadiazol-3-yl)-1(Z)-heptenecarboxamido)-3-(1-methyl-1H-tetrazol-5-yl)-thiomethyl-3-cephem-4-carboxylic acid Preparation in analogy to Example 11 from 1-(5-tert.-butoxycarbonylamino-1,2,4-thiadiazol-3-yl)-1(Z)-heptenecarboxylic acid and 7-amino-3-(1-methyltetrazol-5-yl)thiomethyl-3-cephem-4-carboxylic acid.

EXAMPLE 17

7-(1-(5-Amino-1,2,4-thiadiazol-3-yl)-3-methyl-1(Z)-butenecarboxamido)-3-acetoxymethyl-3-cephem-4-carboxylic acid Preparation in analogy to Example 11 from 1-(5-tert.-butoxycarbonylamino-1,2,4-thiadiazol-3-yl)-3-methyl-1(Z)-butenecarboxylic acid and 3-acetoxymethyl-7-amino-3-cephem-4-carboxylic acid.

EXAMPLE 18

7-(1-(5-Amino-1,2,4-thiadiazol-3-yl)-1(Z)-propenecarboxamido)-3-methyl-3-cephem-4-carboxylic acid Preparation in analogy to Example 11 from 1-(5-tert.-butoxycarbonylamino-1,2,4-thiadiazol-3-yl)-1(Z)-propenecarboxylic acid and 7-amino-3-methyl-3-cephem-4-carboxylic acid. Deviating from Example 11, the 7-amino-3-methyl-3-cephem-4-carboxylic acid is dissolved with the equimolar amount of diisopropylamine, in place of triethylamine, in methylene chloride.

EXAMPLE 19

7-(1-(5-Amino-1,2,4-thiadiazol-3-yl)-1(Z)-propenecarboxamido)-3-aminocarbonyloxymethyl-3-cephem-4-carboxylic acid Preparation in analogy to Example 11 from 1-(5-tert.-butoxycarbonylamino-1,2,4-thiadiazol-3-yl)-1(Z)-propenecarboxylic acid and 7-amino-3-aminocarbonyloxymethyl-3-cephem-4-carboxylic acid. Deviating from Example 11, the 7-amino-3-aminocarbonyloxymethyl-3-cephem-4-carboxylic acid is not dissolved with triethylamine in methylene chloride, but with the equimolar amount of diisoproylamine in anhydrous dimethylformamide, and the resulting solution is added to the mixed carboxylic-sulphonic anhydride in methylene chloride.

For work-up, the mixture is evaporated in vacuo at 0° C., and the residue is taken up in water, extracted with methylene chloride, and ethyl acetate is placed on the aqueous phase which is acidified to pH 2-3.

EXAMPLE 20

7-(5-Amino-1,2,4-thiadiazol-3-yl)-1(Z)-propenecarboxamido-3-cephem-4-carboxylic acid Preparation in analogy to Example 11 from 1-(5-tert.-butoxycarbonylamino-1,2,4-thiadiazol-3-yl)-1(Z)-propenecarboxylic acid and 7-amino-3-cephem-4-carboxylic acid.

EXAMPLE 21

7-(1-(5-Amino-1,2,4-thiadiazol-3-yl)-1(Z)-propenecarboxamido)-3-pyridiniummethyl-3-cephem-4-carboxylate 5 mmol of 1-(5-tert.-butoxycarbonylamino-1,2,4-thiadiazol-3-yl)-1(Z)-propenecarboxylic acid and 5.5 mmol (0.76 ml) of triethylamine are dissolved in 30 ml of anhydrous dimethylformamide, cooled down to −55° C., 5.1 mmol (0.4 ml) of methanesulphonyl chloride are added and the mixture is stirred at −55° C. for half an hour.

The solution thus prepared at −55° C. is poured, all at once, into a solution of 4 mmol (1.16 g) of 7-amino-3-pyridiniummethyl-3-cephem-4-carboxylate and 4 mmol (0.55 ml) of triethylamine in 2 ml of water, the mixture is allowed to warm to room temperature and, during this, the pH is maintained at 8-9.5 with triethylamine.

After 30 minutes the mixture is evaporated in vacuo in a rotary evaporator, the residue is dissolved in a little water, the pH is adjusted to 3-4, and the solution is extracted with ethyl acetate and the aqueous solution is freeze-dried.

The BOC-protected product thus obtained is stirred with 20 ml of trifluoroacetic acid at room temperature for 2 hours, the mixture is evaporated in vacuo in a rotary evaporator, the residue is triturated with ether and the solid is filtered off with suction, washed with methylene chloride containing triethylamine, methylene chloride and acetone and purified as indicated in Example 22.

EXAMPLE 22

7-(1-(5-Amino-1,2,4-thiadiazol-3-yl)-1(Z)-propenecarboxamido)-3-pyridiniummethyl-3-cephem-4-carboxylate 41 mmol (7.5 g) of 1-(5-amino-1,2,4-thiadiazol-3-yl)-1(Z)-propenecarboxylic acid and 4.5 mmol (6.3 ml) of triethylamine are dissolved in 200 ml of anhydrous dimethylformamide, cooled down to −55° C., and 42 mmol (3.3 ml) of methanesulphonyl chloride are added and the mixture is stirred at −55° C. for 30 minutes.

The solution at −55° C. is then added, all at once, to a solution of 31 mmol (11.2 g) of 7-amino-3-pyridiniummethyl-3-cephem-4-carboxylate and 31 mmol (4.3 ml) of triethylamine in 20 ml of water, and the mixture is warmed to room temperature, with vigorous stirring, the pH being maintained at 8-9.5 with triethylamine.

For work-up, the mixture is evaporated in vacuo in a rotary evaporator, and the residue is triturated with ether, and washed several times with methylene chloride and acetone.

In order to remove residual salts and impurities, the product is purified by chromatography on cellulose using acetonitrile/water 5:1 or by absorption on, for example, Diaion HP 20 or XAD 7 and desorption using water/acetone 90:10.

EXAMPLE 23

7-(1-(5-Amino-1,2,4-thiadiazol-3-yl)-1(Z)-butenecarboxamido)-3-pyridiniummethyl-3-cephem-4-carboxylate The preparation is carried out in analogy to Example 21 from 1-(5-tert.-butoxycarbonylamino-1,2,4-thiadiazol-3-yl)-1(Z)-butenecarboxylic acid.

EXAMPLE 24

7-(1-Amino-1,2,4-thiadiazol-3-yl)-1(Z)-pentenecarboxamido)-3-pyridiniummethyl-3-cephem-4-carboxylate The preparation is carried out in analogy to Example 21 from 1-(5-tert.-butoxycarbonylamino-1,2,4-thiadiazol-3-yl)-1(Z)-pentenecarboxylic acid.

EXAMPLE 25

7-(1-(5-Amino-1,2,4-thiadiazol-3-yl)-1(Z)-heptenecarboxamido)-3-pyridiniummethyl-3-cephem-4-carboxylate The preparation is carried out in analogy to Example 21 from 1-(5-tert.-butoxycarbonylamino-1,2,4-thiadiazol-3-yl)-1(Z)-pentenecarboxylic acid.

EXAMPLE 26

7-(1-(5-Amino-1,2,4-thiadiazol-3-yl)-1(Z)-propenecarboxamido)-3-(4-aminocarbonylpyridinium)-methyl-3-cephem-4-carboxylate The preparation is carried out in analogy to Example 21 from 1-(5-tert.-butoxycarbonylamino-1,2,4-thiadiazol-3-yl)-1(Z)-propenecarboxylic acid and 7-amino-3-(4-aminocarbonylpyridinium)methyl-3-cephem-4-carboxylate.

EXAMPLE 27

1-(5-Amino-1,2,4-thiadiazol-3-yl)-1(Z)-propenecarboxylic acid 0.176 mole of 1-(5-tert.-butoxycarbonylamino-1,2,4-thiadiazol-3-yl)-1(Z)-propenecarboxylic acid and 350 ml of trifluoroacetic acid are mixed at 0° C. and stirred at room temperature for 3 hours. The trifluoroacetic acid is removed in vacuo and, with stirring and cooling in ice, saturated aqueous NaHCO₃ solution is added at pH 2 to the residue and then saturated aqueous KHCO₃ solution is added to pH 3.5–4.5. The precipitate is filtered off with suction, washed with water and dried in vacuo over P₂O₅.

EXAMPLE 28

Ethyl α-(5-t-butoxycarbonylamino-1,2,4-thiadiazol-3-yl)acetate

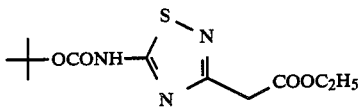

64 g (0.25 mole) of α-(5-t-buxtoxycarbonylamino-1,2,4-thiadiazol-3-yl)acetic acid (European Pat. No. 22,245) in 1.8 liters of ethanol and 5 g of p-toluenesulphonic acid are heated to boiling for 2 hours attached to a water separator filled with molecular sieve (3 Å). The solvent is removed by evaporation in vacuo and the residue is chromatographed on 800 g of silica gel using toluene/acetic acid 1:1, in order to separate off small amounts of aminothiadiazolylacetic acid which was formed at the same time.

Yield >90%, melting point about 90° C.

NMR signals at δ=10.5 (1H), 4.3 (2H), 3.95 (2H), 1.6 (9H) and 1.3 ppm (3H).

EXAMPLE 29

Ethyl α-(5-t-butoxycarbonylamino-1,2,4-thiadiazol-3-yl)-β-hydroxybutyrate

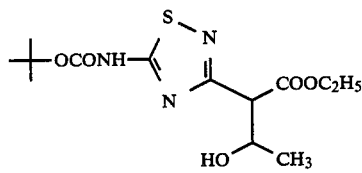

15.9 g (55 mMol) of product from Example 28 in 200 ml of anhydrous ethanol and 9.2 g (110 mMol) of anhydrous sodium acetate and 6.4 ml (5 g) of acetaldehyde are stirred under nitrogen for 3 days. The ethanol is removed in vacuo, the residue is taken up in ethyl acetate, and the solution is washed with water, dried over MgSO₄ and the solvent is removed by evaporation in a rotary evaporator. The residue is chromatographed on 500 g of silica gel using toluene/ethyl acetate 2:1, two fractions being collected which correspond to the diastereomeric mixtures of the erythro and threo forms.

I: Rf values on silica gel TLC plates in toluene/ethyl acetate 1:1=0.40.

Yield: 3.73 g (20.4%).

NMR signals at δ=10.8 (1H), 5.13 (1H), 4.61 (1H), (in CDCl₃) 4.21 (2H), 4.0 (1H), 1.6 (9H), 1.33 (3H) and 1.25 ppm (3H).

II: Rf value in toluene/ethyl acetate 1:1=0.33.

Yield: 6.09 g (33.2%).

NMR signals at δ=10.34 (1H), 4.57 (1H), 4.3–4.15 (3H), 4.11 (1H), 1.6 (9H), 1.28 and 1.25 ppm (6H).

EXAMPLE 30

Ethyl 1-(5-t-butoxycarbonylamino-1,2,4-thiadiazol-3-yl)propene-1-carboxylate

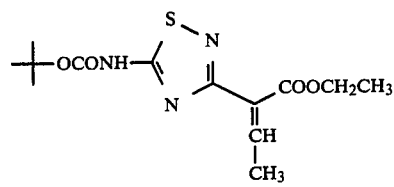

200 ml of thionyl chloride were added to 20.3 g of product II from Example 29 at 0° C., and the mixture was warmed to room temperature and stirred for 45 minutes. The thionyl chloride was now removed in vacuo, the residue was dissolved twice with a little methylene chloride, which was removed in vacuo each time, and the residue was chromatographed on 700 g of silica gel using toluene/ethyl acetate (4:1). 2.54 g (13% of theory) of ethyl Z-1-(5-t-butoxycarbonylamino-1,2,4-thiadiazol-3-yl)propene-1-carboxylate [Rf in toluene-/ethyl acetate 2:1=0.48; NMR signals at δ=9.1 (1H), 7.0 (1H), 4.4 (2H), 2.0 (3H), 1.5 (9H) and 1.3 ppm (3H)] and 6.8 g (35% of theory) of ethyl E-1-(5-t-butoxycarbonylamino-1,2,4-thiadiazol-3-yl)propene-1-carboxylate [Rf in toluene/ethyl acetate 2:1=0.65; NMR signals at δ=9.9 (1H), 7.3 (1H), 4.15 (2H), 1.9 (3H), 1.5 (9H) and 1.15 ppm (3H)] were obtained.

EXAMPLE 31

E-1-(5-t-butoxycarbonylamino-1,2,4-thiadiazol-3-yl)propene-1-carboxylic acid

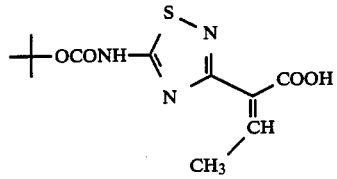

11.5 g (38 mMol) E ester from Example 30 in 84 ml of tetrahydrofuran and 42 ml of 2N NaOH were stirred at 50° C. for 2.5 hours, 200 ml of water were added, the pH was adjusted to 2 with 5N HCl and the mixture was extracted 3×100 ml of ethyl acetate. The combined organic phases were washed with water, dried over MgSO₄ and evaporated. 8.3 g (87%) of yellow crystals of melting point 168° C. (decomposition) remained.

NMR signals at δ=7.3 (1H), 1.9 (3H) and 1.55 ppm (9H).

EXAMPLE 32

Z-1-(5-t-butoxycarbonylamino-1,2,4-thiadiazol-3-yl)propene-1-carboxylic acid

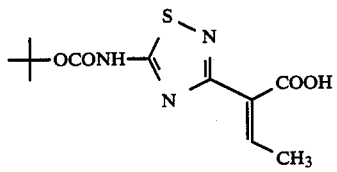

3.33 g (11 mMol) Z ester of Example 30 and 27 ml of THF and 13.5 ml of 2N NaOH were heated at 50° C. for 11 hours. 60 ml of water were added, and the pH was adjusted to 2 with 5N HCl, and the mixture was extracted 3×30 ml of ethyl acetate. The combined organic solutions were dried over MgSO4 and evaporated. The residue was chromatographed with chloroform/methanol (95:5) on 120 g of silica gel, 0.2 g (6.6%) of Z acid [Rf=0.44 in CHCl3/CH3OH (3:1), NMR signals at δ=7.1 (1H), 2.03 (3H) and 1.55 ppm (9H)] and 1.4 g (46%) of E/Z acid mixture were obtained.

EXAMPLE 33

Z-1-(5-t-butoxycarbonylamino-1,2,4-thiadiazol-3-yl)propene-1-carboxylic acid

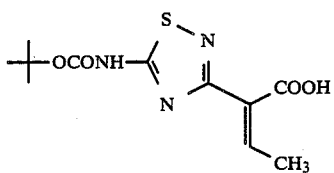

8.3 g (29 mMol) of E-1-(5-t-butoxycarbonylamino-1,2,4-thiadiazol-3-yl)propene-1-carboxylic acid were dissolved in 40 ml of DMF and the solution was added to a solution of 10 g of potassium t-butylate in 30 ml of DMF at 0° C., whereupon the internal temperature rose to 30° C. The mixture was stirred for 15 minutes, 300 ml of water were poured in and the pH was adjusted to 2 with 1N HCl. The mixture was extracted 2×ethyl acetate and the combined organic phases were washed with water, dried over MgSO4 and evaporated in vacuo. 8.0 g (96%) of E/Z mixture ~1:2.

The E and Z acids were separated by counter-current partition between ethyl acetate and water at pH 6.6, the Z acid migrating with the aqueous phase and the E acid migrating with the ethyl acetate phase. Yield virtually quantitative.

EXAMPLE 34

Z-1-(5-amino-1,2,4-thiadiazol-3-yl)propene-1-carboxylic acid

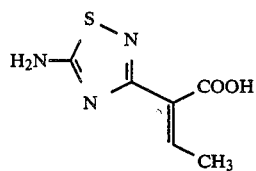

340 mg (1.2 mMol) of Z-1-(5-t-butoxycarbonylamino-1,2,4-thiadiazol-3-yl)propene-1-carboxylic acid were dissolved in 4 ml of trifluoroacetic acid at 0° C. and stirred at 0° C. for 2 hours. The trifluoroacetic acid was now removed in vacuo, and the residue was dissolved 2×in CH2Cl2 which was again removed in vacuo each time. The residue was dissolved in 5 ml of water, the pH was adjusted to 4 with 1N NaOH, and the mixture was extracted 3×20 ml of ethyl acetate, which was discarded. The evaporated aqueous phase was filtered through 25 g of silica gel using CHCl3/CH3OH (3:1) and the solvent was evaporated.

Yield 120 mg=54%.

NMR signals at δ=6.9 (1H) and 1.95 ppm (3H).

EXAMPLE 35

Ethyl α-(5t-butoxycarbonylamino-1,2,4-thiadiazol-3-yl)-β-hydroxyvalerate

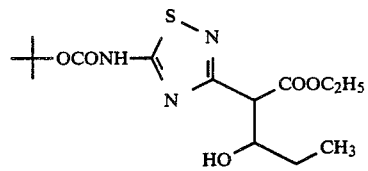

1.0 g (3.5 mMol) of product from Example 28 were reacted with 0.76 ml (~10 mMol) of propanol for 5 days in the manner described in Example 29 and the separated into the erythro and threo forms by chromatography on silica gel using toluene/ethyl acetate 4:1.

Product I [Rf=0.62 in toluene/ethyl acetate 1:1;
NMR signals (DMF-d7) at δ=9.3 (1H), 4.4 (1H), 4.28 (1H), 4.17 (2H), 4.01 (1H), 1.57 (9H), 1.48 (2H), 1.24 (3H) and 1.00 ppm (3H)]; 230 mg=19% of theory.

Product II [Rf=0.53 in toluene/ethyl acetate 1:1;
NMR signals (DNF-d7) at δ=9.0 (1H), 4.2 (3H), 4.03 (1H), 3.8 (1H), 1.57 (9H), 1.54 (2H), 1.25 (3H) and 1.00 ppm 3H]: 320 mg=26% of theory.

EXAMPLE 36

Ethyl 1-(5-t-butoxycarbonylamino-1,2,4-thiadiazol-3-yl)-1-butene-1-carboxylate

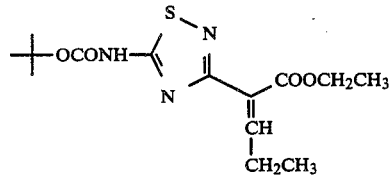

1.1 g (3.2 mMol) of product I from Example 35 were warmed to 24° C. with 0.44 ml of thionyl chloride in 11 ml of CH2Cl2 for 30 minutes. The solvent was now removed in vacuo, and CH2Cl2 was added twice more, being distilled out each time in vacuo. The residue was chromatographed on 40 g of silica gel using toluene/ethyl acetate (4:1). 0.49 g of E/Z mixture of the title compound and 370 mg of the E form of the title compound were obtained.

NMR signals (in CDCl3) at δ=9.57 (1H), 7.14 (1H), 4.15 (2H), 2.3 (2H), 1.55 (9H), 1.2 (3H) and 1.05 ppm (3H).

EXAMPLE 37

Ethyl 1-(5-t-butoxycarbonylamino-1,2,4-thiadiazol-3-yl)-1-butene-1-carboxylate

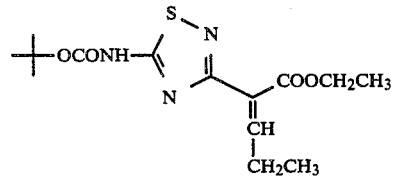

1.95 g (5.6 mMol) of product II from Example 35 were reacted with thionyl chloride and chromatographed on silica gel in the manner described in Example 36. 0.63 g (34%) of Z title ester [Rf value in toluene-/ethyl acetate 2:1 on silica gel 0.68; NMR signals (in CDCl$_3$) at δ=8.8 (1H), 6.9 (1H), 4.34 (2H), 2.4 (2H), 1.57 (9H), 1.25 (3H) and 1.04 ppm (3H)] and 0.61 g (33%) of E title ester of Rf value 0.56 in toluene/ethyl acetate 2:1 on silica gel were obtained.

EXAMPLE 38

Ethyl α-(5-t-butoxycarbonylamino-1,2,4-thiadiazol-3-yl)-β-hydroxycaproate

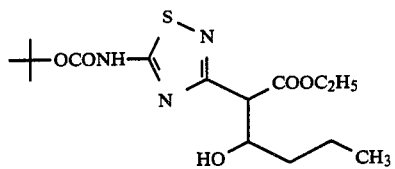

1.0 g (3.5 mMol) of product from Example 28 were reacted with 0.9 ml (~10 mMol) of n-butanal for 5 days in the manner described in Example 29 and then purified by chromatography on silica gel. Yield 0.17 g (14% of theory).

NMR signals (in CDCl$_3$) at δ=10.0 (1H), 4.34 (1H), 4.18 (2H), 4.08 (1H), 3.98 (1H), 1.57 (9H), 1.6–1.3 (4H), 1.22 (3H) and 0.9 ppm (3H).

EXAMPLE 39

Ethyl α-(5-t-butoxycarbonylamino-1,2,4-thiadiazol-3-yl)-β-hydroxyhexane-1-carboxylate

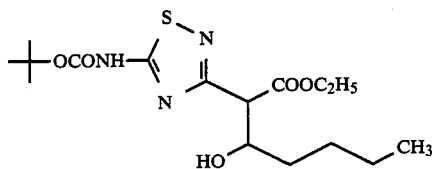

1.0 g (3.5 mMol) of product from Example 28 were reacted with 1.1 g (~10 mMol) of n-pentanal for 9 days in the manner described in Example 29 and, after aqueous work-up, the product was isolated from the ethyl acetate extract. A 1:1 mixture of the erythro and threo forms resulted.

NMR signals (in CDCl$_3$) at δ=9.8 (1H), 4.34 (1H), 4.2 (3H), 4.05 (1H), 1.7–1.3 (9H), 1.58 (9H) and 0.9 ppm (3H).

EXAMPLE 40

Ethyl α-(5-t-butoxycarbonylamino-1,2,4-thiadiazol-3-yl)-β-hydroxycaprylate

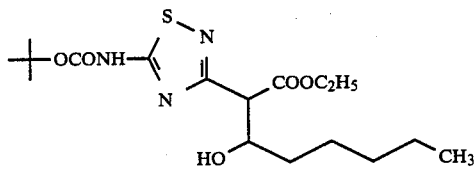

1.0 g (3.5 mMol) of product from Example 28 were reacted with 1.26 ml (~10 mMol) of n-hexanal for 9 days in the manner described in Example 29. Yield of erythro/threo mixture of the title compound: 1.1 g (~80%).

NMR signals (in CDCl$_3$) at δ=9.9 (1H), 4.33 (1H), 4.2 (2H), 4.04 (1H), 1.8–1.1 (11H), 1.58 (9H) and 0.9 ppm (3H).

EXAMPLE 41

Ethyl α-(5-t-butoxycarbonylamino-1,2,4-thiadiazol-3-yl)-β-hydroxyoctanecarboxylate

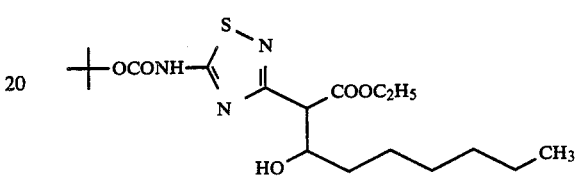

1.0 g (3.5 mMol) of product from Example 28 were reacted with 1.46 ml (~10 mMol) of n-heptanal in the manner described in Example 29. Yield of erythro/threo mixture of the title compound: 1.4 g.

NMR signals (in CDCl$_3$) at δ=10.0 (1H), 4.37 (1H), 4.22 (2H), 4.08 (1H), 1.8–1.2 (13H), 1.6 (9H) and 0.9 ppm (3H).

EXAMPLE 42

Ethyl α-(5-t-butoxycarbonylamino-1,2,4-thiadiazol-3-yl)-β-hydroxy-δ-phenylvalerate

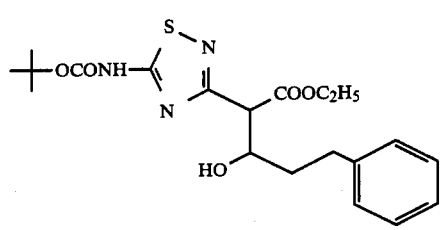

1.0 g (3.5 mMol) of product from Example 28 were reacted with 1.4 ml (~10 mMol) of dihydrocinnamaldehyde for 5 days in the manner described in Example 29 and, after working up by aqueous extraction, the product was chromatographed on 25 g of silica gel using toluene/ethyl acetate (4:1) and separated into the erythro and threo forms.

Product I [Rf=0.76 in toluene/ethyl acetate 1:1,

NMR signals (in CDCl$_3$) at δ=10.26 (1H), 7.35–7.1 (5H), 4.8 (1H), 4.43 (1H), 4.2 (2H), 4.1 (1H), 2.95–2.6 (2H), 1.76 (2H), 1.55 (9H) and 1.2 ppm (3H)]: 0.13 g=9% of theory.

Product II [Rf=0.69 in toluene/ethyl acetate 1:1,

NMR signals (in CDCl$_3$) at δ=9.7 (1H), 7.1 (5H), 4.5–3.8 (5H), 3.0–2.45 (2H), 2.0–1.6 (2H), 1.5 (9H) and 1.17 ppm (3H)]: 0.17 g (11% of theory).

EXAMPLE 43

Ethyl α-(5-t-butoxycarbonylamino-1,2,4-thiadiazol-3-yl)-β-hydroxy-β-(2-furyl)propionate

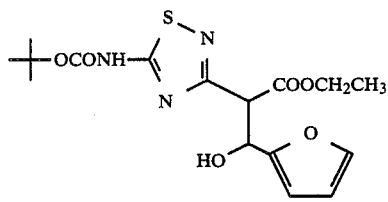

1.0 g (3.5 mMol) of product from Example 28 were reacted with 0.87 ml (~10 mMol) of furfural for 5 days in the manner described in Example 29 and worked up by aqueous extraction.

Yield: 1 g (75% of theory). Mixture of the erythro and threo forms.

NMR signals (in CDCl$_3$) at δ=10 (1H), 7.25 (1H), 6.2 (2H), 5.5 (1H), 4.5 (1H), 4.18 (2H), 1.57 (9H) and 1.22 ppm (3H). All the signals are split appropriate for the ratio of isomers (5:4).

EXAMPLE 44

E-1-(5-t-butoxycarbonylamino-1,2,4-thiadiazol-3-yl)-1-butene-1-carboxylic acid

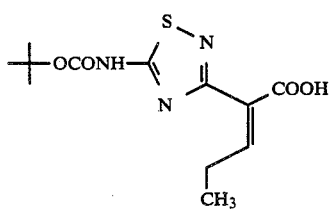

480 mg of E ester from Example 37 were reacted in the manner described in Example 31.

Yield 420 mg=95%.

NMR signals (in CD$_3$OD) at δ=7.16 (1H), 2.2 (2H), 1.5 (9H) and 1.02 ppm (3H).

EXAMPLE 45

Z-1-(5-t-butoxycarbonylamino-1,2,4-thiadiazol-3-yl)-1-butene-1-carboxylic acid

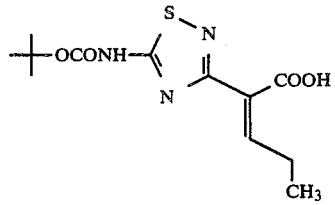

410 mg of E acid from Example 44 were isomerized with potassium t-butylate in the manner described in Example 33, a 9:1 mixture of Z and E acids being obtained (340 mg).

150 mg (37%) of pure Z acid and 110 mg of E/Z mixture (1:9) were obtained by chromatography on 20 g of silica gel using CHCl$_3$/CH$_3$OH 6:1.

Z acid:

NMR signals (in CD$_3$OD) at δ=6.97 (1H), 2.4 (2H), 1.5 (9H) and 1.1 ppm (3H).

EXAMPLE 46

7-[1-(5-t-butoxycarbonylamino-1,2,4-thiadiazol-3-yl)-1-(Z)-propenecarboxamido]-3-pyridiniummethyl-3-cephem-4-carboxylate

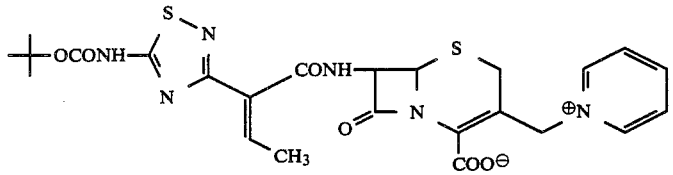

672 μl (3.9 mMol) of ethyldiisopropylamine were added to 1 g (3.5 mMol) of Z acid from Example 33 in 9 ml of dimethylformamide under N$_2$ and the mixture was cooled to −55° C. 282 μl (3.6 mMol) of mesyl chloride were added, with stirring, and the mixture was stirred at −55° C. for 3 minutes. Then a solution of 970 mg (2.7 mMol) of 3'-deacetoxypyridiniummethyl 7-aminocephalosporanate hydrochloride hydrate in 1.1 ml of water (pH adjusted to 7 with triethylamine) was added and the pH was maintained at 9.3 by addition of triethylamine. The mixture was allowed to reach room temperature and stirred for 20 minutes. It was poured into 130 ml of acetone, stirred for 1 hour, and the solid was filtered off with suction, stirred in CH$_2$Cl$_2$, filtered off with suction and washed with CH$_2$Cl$_2$ and ether.

Yield 17% of theory=270 mg.

An equal amount of ether was added to the combined organic phases and the precipitated oil was converted into the form of a powder by digestion with anhydrous ether.

Yield 1.27 g (83% of theory). Product is homogeneous by TLC.

NMR signals (in D$_2$O) at δ=9.0 (2H), 8.6 (1H), 8.13 (2H), 7.07 L (1H), 5.94 (1H), 5.59 (1H), 5.39 (1H), 5.33 (1H), 3.7 (1H), 3.3 (1H), 1.98 (3H) and 1.54 ppm (9H).

EXAMPLE 47

7-[1-(5-amino-1,2,4-thiadiazol-3-yl)-1-(Z)-propenecarboxamido]-3-pyridiniummethyl-3-cephem-4-carboxylic acid trifluoroacetate

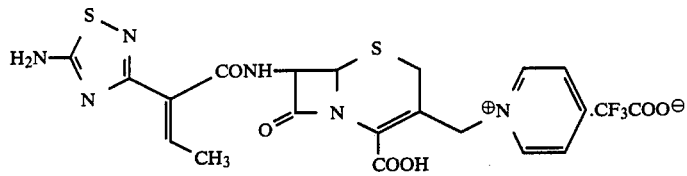

1.2 g (~2 mMol) of cephalosporin from Example 46 were dissolved in trifluoroacetic acid (4.7 mMol) at 0° C. and the solution was allowed to stand at room temperature for 1 hour. The trifluoroacetic acid was removed in vacuo, and 3×10 ml of methylene chloride were added and removed in vacuo each time. The residue was thoroughly mixed with anhydrous ether several times and the remaining powder was purified on 15 g of silica gel using $CH_3L$ $CN/H_2O$ 3:2.

Yield: 0.9 g=69% of theory, homogeneous by TLC.
IR bands at 3600–2500, 1765, 1660, 1620, 1195 and 720 cm$^{-1}$ (in Nujol).

NMR signals (in $D_2O$) at δ=9.0 (2H), 8.62 (1H), 8.13 (2H), 6.94(1H), 5.94(1H), 5.68 (1H). 5.40 (1H), 5.33 (1H), 3.7 (1H), 3.3 (1H) and 1.96 ppm (3H).

EXAMPLE 48

7-[1-(5-t-butoxycarbonylamino-1,2,4-thiadiazol-3-yl)-(Z)-1-butene-1-carboxamido]-3-pyridiniummethyl-3-cephem-4-carboxylate

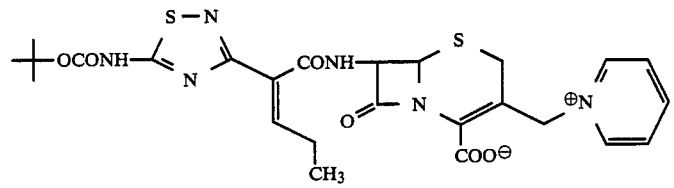

150 mg (0.5 mMol) of Z acid from Example 45 were reacted with 3'-deacetoxypyridiniummethyl 7-aminocephalosporin hydrochloride hydrate in the manner described in Example 46.

Yield: 41 mg (18% of theory).
NMR signals (in $D_2O$) at δ=9.0 (2H), 8.6 (1H), 8.15 (2H), 7.0 (1H), 5.9 (1H), 5.6 (1H), 5.4 (1H), 5.3 (1H), 3.7 (1H), 3.3 (1H), 2.4 (2H), 1.55 (9H) and 1.1 ppm (3H).

EXAMPLE 49

7-[1-(5-amino-1,2,4-thiadiazol-3-yl)-(Z)-1-butene-1-carboxamido]-3-pyridiniummethyl-3-cephem-4-carboxylic acid trifluoroacetate

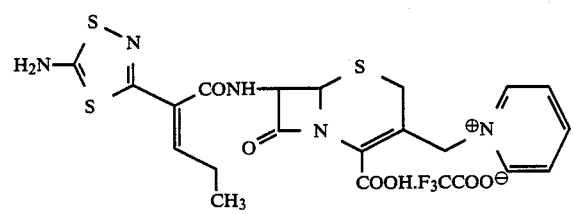

260 mg (0.45 mMol) of cephalosporin from Example 48 were reacted with trifluoroacetic acid in the manner described in Example 47.

Yield: 130 mg=50% of theory.
NMR signals (in $D_2O$) at δ=9.0 (2H), 8.6 (1H), 8.1 (2H), 6.9 (1H), 5.9 (1H), 5.7 (1H), 5.4 (1H), 5.3 (1H), 3.7 (1H), 3.3 (1H), 2.4 (2H) and 1.1 ppm (3H).

It is understood that the specification and examples are illustrative but not limitative of the present invention and that other embodiments within the spirit and scope of the invention will suggest themselves to those skilled in the art.

We claim:

1. A compound of the formula

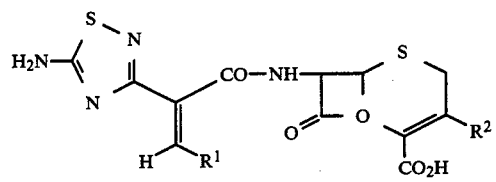

in which
$R^1$ denotes hydrogen, $C_1$–$C_{12}$-alkyl, phenyl or a halogen substituted phenyl ring,
$R^2$ represents hydrogen, $C_1$–$C_4$-alkyl, $C_1$–$C_4$-alkenyl, halogen, $C_1$–$C_4$-alkoxy, $C_1$–$C_4$-alkylthio, hydroxymethyl, formyloxymethyl, $C_1$–$C_4$-alkylcarbonyloxymethyl, aminocarbonyloxymethyl, pyridiniummethyl, 4-carbamoylpyridiniummethyl, 4-sulphonylethylpyridiniummethyl, 4-carboxylmethylpyridiniummethyl or heterocyclylthiomethyl, heterocyclyl repesenting a radical of the formula

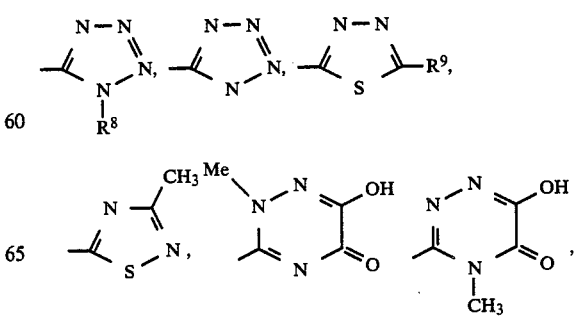

-continued

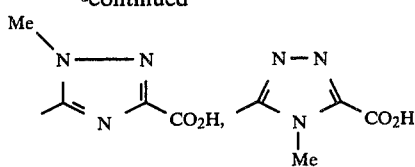

wherein
R[8] denotes hydrogen, methyl, 2-dimethylaminoethyl, carboxymethyl, sulphomethyl, carboxyethyl or sulphoethyl and
R[9] denotes hydrogen or methyl,
or a pharmaceutically tolerated salt or ester thereof.

2. A compound, salt or ester according to claim 1, in which R[1] represents $C_1$-$C_{12}$-alkyl, phenyl or halogen-substituted phenyl.

3. A compound, salt or ester according to claim 1, in which R[2] represents

H, Cl, $OCH_3$, $-CH_2OCOCH_3$, $CH_2-O-CONH_2$,

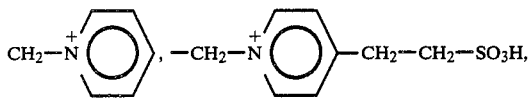

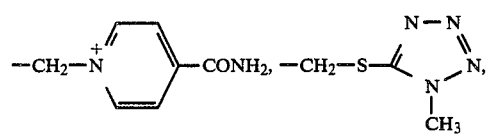

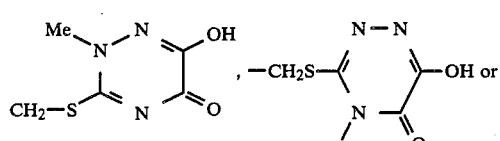

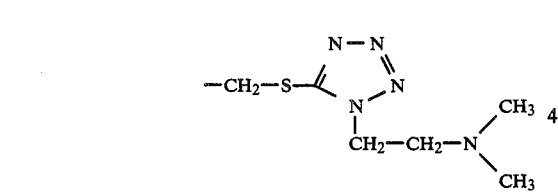

4. A compound according to claim 1, wherein such compound is 7-(1-(5-amino-1,2,4-thiadiazol-3-yl)-1(Z)-propenecarboxamido-3-acetoxymethyl)-3-cephem-4-carboyxlic acid of the formula

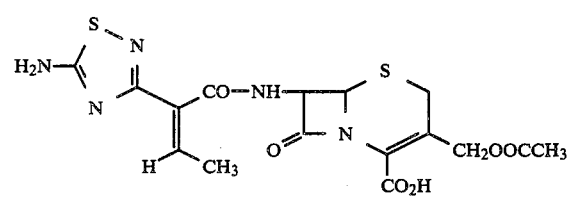

or a pharmaceutically tolerated salt or ester thereof.

5. A compound according to claim 1, wherein such compound is 7-(1-(5-amino-1,2,4-thiadiazol-3-yl)-1(Z)-propenecarboxamido)-3-(1-methyl-1H-tetrazol-5-yl)-thiomethyl-3-cephem-4-carboxylic acid of the formula

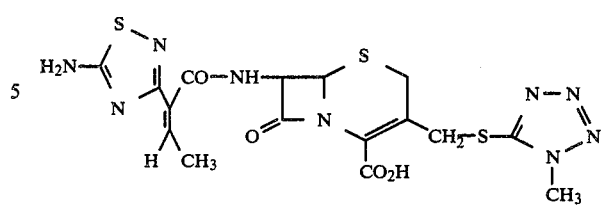

or a pharmaceutically tolerated salt or ester thereof.

6. A compound according to claim 1, wherein such compound is 7-(1-(5-amino-1,2,4-thiodiazol-3-yl)-1(Z)-propenecarboxamido)-3-aminocarbonyloxymethyl-3-cephem-4-carboxylic acid of the formula

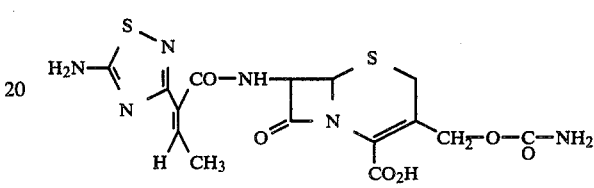

or a pharmaceutically tolerated salt or ester thereof.

7. A compound according to claim 1, wherein such compound is 7-(5-amino-1,2,4-thiadiazol-3-yl)-1(Z)-propenecarboxamido-3-cephem-4-carboxylic acid of the formula

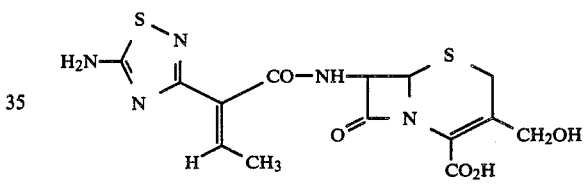

or a pharmaceutically tolerated salt or ester thereof.

8. A compound according to claim 1, wherein such compound is 7-(1-(5-amino-1,2,4-thiadiazol-3-yl)-1(Z)-propenecarboxamido)-3-pyridiniummethyl-3-cephem-4-carboxylate of the formula

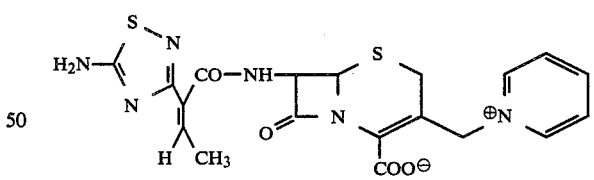

or a pharmaceutically tolerated salt or ester thereof.

9. An antibacterial composition comprising an antibacterially effective amount of a compound, salt or ester according to claim 1 in admixture with a diluent.

10. A unit dose of a composition according to claim 9 in the form of a tablet, capsule or ampule.

11. A method of combating bacteria in a patient which comprises administering to such patient an antibacterially effective amount of a compound, salt or ester according to claim 1.

12. The method according to claim 11, wherein such compound is
7-(1-(5-amino-1,2,4-thiadiazol-3-yl)-1(Z)-propene-carboxamido-3-acetoxymethyl)-3-cephem-4-carboxylic acid, 7-(1-(5-amino-1,2,4-thiodiazol-3-yl)-1(Z)-propenecarboxamido)-3-(1-methyl-1H-tetrazol-5-yl)-thiomethyl-3-cephem-4-carboxylic acid, 7-(1-5(5-amino-12,4-thiodiazol-3-yl)-1(Z)-propenecarboxamido)-3-aminocarbonyloxymethyl-3-cephem-4-carboxylic acid, 7-(5-amino-1,2,4-thiadiazol-3-71)-1(Z)-propenecarboxamido-3-cephem-4-carboxylic acid or 7-(1-(5-amino-1,2,4-thiadiazol-3-yl)-1(Z)-propenecarboxamido)-3-pyridiniummethyl-3-cephem-4-carboxylate, or a pharmaceutically acceptable salt or ester thereof.

* * * * *